United States Patent
Beaurain et al.

(10) Patent No.: US 7,682,396 B2
(45) Date of Patent: Mar. 23, 2010

(54) INTERVERTEBRAL DISC PROSTHESIS

(75) Inventors: Jacques Beaurain, Saulon la Chapelle (FR); Jean-Marc Fuentes, Grabels (FR); Jean-Marc Vital, Bordeaux (FR); Thierry Dufour, Olivet (FR); Jean Huppert, L'Etrat (FR)

(73) Assignee: LDR Medical, Troyes (FR)

( * ) Notice: Subject to any disclaimer, the term of this patent is extended or adjusted under 35 U.S.C. 154(b) by 412 days.

(21) Appl. No.: 10/533,846

(22) PCT Filed: Oct. 31, 2003

(86) PCT No.: PCT/IB03/04872

§ 371 (c)(1),
(2), (4) Date: Nov. 11, 2005

(87) PCT Pub. No.: WO2004/041129

PCT Pub. Date: May 21, 2004

(65) Prior Publication Data

US 2006/0155377 A1  Jul. 13, 2006

(30) Foreign Application Priority Data

Nov. 5, 2002 (FR) .................................. 02 13833

(51) Int. Cl.
*A61F 2/44* (2006.01)

(52) U.S. Cl. .................. 623/17.14; 623/17.15

(58) Field of Classification Search ... 623/17.11–17.16; 606/61, 246, 279
See application file for complete search history.

(56) References Cited

U.S. PATENT DOCUMENTS

| | | | |
|---|---|---|---|
| 566,360 | A | 8/1896 | White |
| 1,436,573 | A | 11/1922 | Choppinet et al. |
| 2,836,442 | A | 5/1958 | Moskovitz |
| 3,325,197 | A | 6/1967 | Wehner |

(Continued)

FOREIGN PATENT DOCUMENTS

DE  2263842  7/1974

(Continued)

OTHER PUBLICATIONS

A biolological basis for instantaneous centres of rotation of the vertebral column, N. Bouduk, B. Amevo, M. Pearcy, Proc Insititution Mechanical Engineers, Jun. 16, 1995, pp. 177-183.

(Continued)

*Primary Examiner*—Thomas C Barrett
*Assistant Examiner*—Andrew Yang
(74) *Attorney, Agent, or Firm*—Civins Denko Coburn & Lauff LLP

(57) ABSTRACT

The present invention relates to an intervertebral disk prosthesis comprising at least three parts including a first plate, referred to as the upper plate (1), a second plate, referred to as the lower plate (2), and a core (3), the upper surface of the core (3) being in contact with at least part (10) of the lower surface of the upper plate (1) and the lower surface of the core (3) being in contact with at least part of the upper surface of the lower plate (2), and the lower plate (1) being movable at least with respect to the core (3), characterised in that there are cooperation means between the lower to plate (2) and the core (3), so as to limit or eliminate translation movements of the core (3) with respect to the lower plate (2) along an axis substantially parallel to the lower plate (2), and to limit or eliminate rotation movements of the core (3) with respect to the lower plate (2), around an axis substantially perpendicular to the lower plate (2), the planes passing through the upper (1) is and lower (2) plates forming a substantially constant angle.

31 Claims, 4 Drawing Sheets

U.S. PATENT DOCUMENTS

Figure 9A:
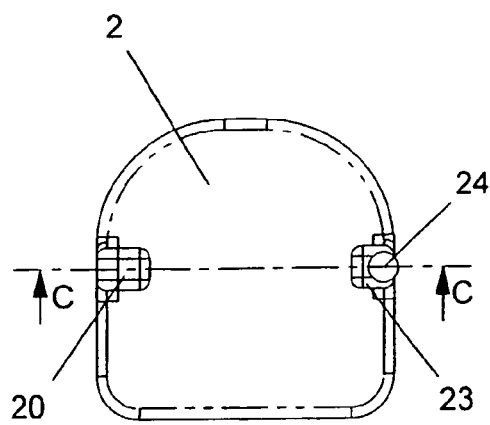

| | | |
|---|---|---|
| 3,857,642 A | 12/1974 | Miller |
| 3,958,278 A | 5/1976 | Lee et al. |
| 4,074,542 A | 2/1978 | Hankosky et al. |
| 4,085,466 A | 4/1978 | Goodfellow et al. |
| 4,309,777 A | 1/1982 | Patil |
| 4,349,921 A | 9/1982 | Kuntz |
| 4,655,778 A | 4/1987 | Koeneman |
| 4,714,469 A | 12/1987 | Kenna |
| 4,756,711 A | 7/1988 | Mai et al. |
| 4,759,766 A | 7/1988 | Buettner-Janz et al. |
| 4,759,769 A | 7/1988 | Hedman et al. |
| 4,787,908 A | 11/1988 | Wyss et al. |
| 4,863,476 A | 9/1989 | Shepperd |
| 4,874,389 A | 10/1989 | Downey |
| 4,892,545 A | 1/1990 | Day et al. |
| 4,911,718 A | 3/1990 | Lee et al. |
| 4,932,975 A | 6/1990 | Main |
| 4,946,378 A | 8/1990 | Hirayama et al. |
| 4,955,908 A | 9/1990 | Frey et al. |
| 4,955,916 A | 9/1990 | Carignan et al. |
| 4,997,432 A | 3/1991 | Keller |
| 5,002,576 A | 3/1991 | Fuhrmann et al. |
| 5,041,139 A | 8/1991 | Branemark |
| 5,071,437 A | 12/1991 | Steffee |
| 5,122,130 A | 6/1992 | Keller |
| 5,123,926 A | 6/1992 | Pisharodi |
| 5,171,281 A | 12/1992 | Parsons et al. |
| 5,192,327 A | 3/1993 | Brantigan |
| 5,197,986 A | 3/1993 | Mikhail |
| 5,246,458 A | 9/1993 | Graham |
| 5,258,031 A | 11/1993 | Salib et al. |
| 5,290,312 A | 3/1994 | Kojimoto et al. |
| 5,306,309 A | 4/1994 | Wagner et al. |
| 5,314,477 A | 5/1994 | Marnay |
| 5,358,526 A | 10/1994 | Tornier |
| 5,370,697 A | 12/1994 | Baumgartner |
| 5,397,364 A | 3/1995 | Kozak et al. |
| 5,401,269 A | 3/1995 | Buettner-Janz et al. |
| 5,425,773 A | 6/1995 | Boyd et al. |
| 5,507,816 A | 4/1996 | Bullivant |
| 5,534,029 A | 7/1996 | Shima |
| 5,534,030 A | 7/1996 | Navarro et al. |
| 5,545,229 A | 8/1996 | Parsons et al. |
| 5,556,431 A | 9/1996 | Buettner-Janz et al. |
| 5,562,738 A | 10/1996 | Boyd et al. |
| 5,571,109 A | 11/1996 | Bertagnoli |
| 5,609,636 A | 3/1997 | Kohrs et al. |
| 5,645,596 A | 7/1997 | Kim |
| 5,674,294 A | 10/1997 | Bainville et al. |
| 5,676,701 A | 10/1997 | Yuan et al. |
| 5,676,702 A | 10/1997 | Ratron |
| 5,683,465 A | 11/1997 | Shinn et al. |
| 5,702,450 A | 12/1997 | Bisserie |
| 5,702,472 A | 12/1997 | Huebner |
| 5,722,977 A | 3/1998 | Wilhelmy |
| 5,741,253 A | 4/1998 | Michelson |
| 5,766,252 A | 6/1998 | Henry et al. |
| 5,772,661 A | 6/1998 | Michelson |
| 5,776,199 A | 7/1998 | Michelson |
| 5,782,832 A | 7/1998 | Larsen et al. |
| 5,782,919 A | 7/1998 | Zdeblick et al. |
| 5,797,909 A | 8/1998 | Michelson |
| 5,824,094 A | 10/1998 | Serhan et al. |
| 5,827,328 A | 10/1998 | Buttermann |
| 5,865,848 A | 2/1999 | Baker |
| 5,888,224 A | 3/1999 | Beckers et al. |
| 5,888,226 A | 3/1999 | Rogozinski |
| 5,893,889 A | 4/1999 | Harrington |
| 5,895,428 A | 4/1999 | Berry |
| 5,899,941 A | 5/1999 | Nishijima |
| 5,984,967 A | 11/1999 | Zdeblick et al. |
| 6,001,130 A | 12/1999 | Bryan et al. |
| 6,010,502 A | 1/2000 | Bagby |
| 6,033,438 A | 3/2000 | Bianchi et al. |
| 6,039,763 A | 3/2000 | Shelokov |
| 6,045,552 A | 4/2000 | Zucherman et al. |
| 6,063,121 A | 5/2000 | Xavier et al. |
| 6,080,158 A | 6/2000 | Lin |
| 6,093,205 A | 7/2000 | McLeod et al. |
| 6,096,038 A | 8/2000 | Michelson |
| 6,096,080 A | 8/2000 | Nicholson et al. |
| 6,113,637 A | 9/2000 | Gill et al. |
| 6,113,638 A | 9/2000 | Williams et al. |
| 6,136,031 A | 10/2000 | Middleton |
| 6,146,421 A | 11/2000 | Gordon et al. |
| 6,146,422 A | 11/2000 | Lawson |
| 6,149,650 A | 11/2000 | Michelson |
| 6,156,067 A | 12/2000 | Bryan et al. |
| 6,179,873 B1 * | 1/2001 | Zientek ................. 623/17.11 |
| 6,179,874 B1 | 1/2001 | Cauthen |
| 6,193,757 B1 | 2/2001 | Foley et al. |
| 6,206,922 B1 | 3/2001 | Zdeblick et al. |
| 6,210,412 B1 | 4/2001 | Michelson |
| 6,224,595 B1 | 5/2001 | Michelson |
| 6,228,118 B1 | 5/2001 | Gordon |
| 6,231,609 B1 | 5/2001 | Mehdizadeh |
| 6,245,072 B1 | 6/2001 | Zdeblick et al. |
| 6,258,094 B1 | 7/2001 | Nicholson et al. |
| 6,261,293 B1 | 7/2001 | Nicholson et al. |
| 6,264,656 B1 | 7/2001 | Michelson |
| 6,267,763 B1 | 7/2001 | Castro |
| 6,270,498 B1 | 8/2001 | Michelson |
| 6,277,149 B1 | 8/2001 | Boyle et al. |
| 6,283,998 B1 | 9/2001 | Eaton |
| 6,296,664 B1 | 10/2001 | Middleton |
| 6,306,170 B2 | 10/2001 | Ray |
| 6,315,797 B1 | 11/2001 | Middleton |
| 6,319,257 B1 | 11/2001 | Carignan et al. |
| 6,344,057 B1 | 2/2002 | Rabbe et al. |
| 6,364,880 B1 | 4/2002 | Michelson |
| 6,368,350 B1 * | 4/2002 | Erickson et al. .......... 623/17.14 |
| 6,371,988 B1 | 4/2002 | Pafford et al. |
| 6,375,655 B1 | 4/2002 | Zdeblick et al. |
| 6,387,130 B1 | 5/2002 | Stone et al. |
| 6,395,035 B2 | 5/2002 | Bresina et al. |
| 6,402,750 B1 | 6/2002 | Atkinson et al. |
| 6,402,785 B1 | 6/2002 | Zdeblick et al. |
| 6,409,765 B1 | 6/2002 | Bianchi et al. |
| 6,413,278 B1 | 7/2002 | Marchosky |
| 6,416,551 B1 | 7/2002 | Keller |
| 6,419,704 B1 | 7/2002 | Ferree |
| 6,419,706 B1 * | 7/2002 | Graf ....................... 623/17.16 |
| 6,423,095 B1 | 7/2002 | Van Hoeck et al. |
| 6,440,168 B1 | 8/2002 | Cauthen |
| 6,447,512 B1 | 9/2002 | Landry et al. |
| 6,447,547 B1 | 9/2002 | Michelson |
| 6,468,310 B1 | 10/2002 | Ralph et al. |
| 6,471,724 B2 | 10/2002 | Zdeblick et al. |
| 6,478,823 B1 | 11/2002 | Michelson |
| 6,482,234 B1 | 11/2002 | Weber et al. |
| 6,506,216 B1 | 1/2003 | McCue et al. |
| 6,514,260 B1 | 2/2003 | Zdeblick et al. |
| 6,517,580 B1 | 2/2003 | Ramadan et al. |
| 6,520,996 B1 | 2/2003 | Manasas et al. |
| 6,524,312 B2 | 2/2003 | Landry et al. |
| 6,527,804 B1 | 3/2003 | Gauchet et al. |
| 6,527,806 B2 | 3/2003 | Ralph et al. |
| 6,540,785 B1 | 4/2003 | Gill et al. |
| 6,579,291 B1 | 6/2003 | Keith et al. |
| 6,582,468 B1 | 6/2003 | Gauchet et al. |
| 6,592,624 B1 | 7/2003 | Fraser et al. |
| 6,599,320 B1 | 7/2003 | Kuslich et al. |
| 6,607,558 B2 | 8/2003 | Kuras |
| 6,610,089 B1 | 8/2003 | Liu et al. |

| | | |
|---|---|---|
| 6,610,092 B2 | 8/2003 | Ralph et al. |
| 6,610,093 B1 * | 8/2003 | Pisharodi ................. 623/17.15 |
| 6,613,091 B1 | 9/2003 | Zdeblick et al. |
| 6,616,671 B2 | 9/2003 | Landry et al. |
| 6,641,614 B1 | 11/2003 | Wagner et al. |
| 6,645,206 B1 | 11/2003 | Zdeblick et al. |
| 6,645,249 B2 | 11/2003 | Ralph et al. |
| 6,652,533 B2 | 11/2003 | O'Neil |
| 6,652,586 B2 | 11/2003 | Hunter et al. |
| 6,656,224 B2 | 12/2003 | Middleton |
| 6,669,730 B2 | 12/2003 | Ralph et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,679,915 B1 | 1/2004 | Cauthen |
| 6,682,562 B2 | 1/2004 | Viart et al. |
| 6,695,851 B2 | 2/2004 | Zdeblick et al. |
| 6,695,882 B2 | 2/2004 | Bianchi et al. |
| 6,706,068 B2 | 3/2004 | Ferree |
| 6,709,439 B2 | 3/2004 | Rogers et al. |
| 6,719,794 B2 | 4/2004 | Gerber et al. |
| 6,723,127 B2 | 4/2004 | Ralph et al. |
| 6,726,720 B2 | 4/2004 | Ross et al. |
| 6,730,088 B2 | 5/2004 | Yeh |
| 6,733,504 B2 | 5/2004 | Lin et al. |
| 6,733,532 B1 | 5/2004 | Gauchet et al. |
| 6,733,535 B2 | 5/2004 | Michelson |
| 6,736,850 B2 | 5/2004 | Davis |
| 6,740,117 B2 | 5/2004 | Ralph et al. |
| 6,740,118 B2 | 5/2004 | Eisermann et al. |
| 6,749,635 B1 | 6/2004 | Bryan |
| 6,755,841 B2 | 6/2004 | Fraser et al. |
| 6,764,512 B2 | 7/2004 | Keller |
| 6,764,515 B2 | 7/2004 | Ralph et al. |
| 6,767,367 B1 | 7/2004 | Michelson |
| 6,770,074 B2 | 8/2004 | Michelson |
| 6,770,095 B2 | 8/2004 | Grinberg et al. |
| 6,793,678 B2 | 9/2004 | Hawkins |
| 6,800,093 B2 | 10/2004 | Nicholson et al. |
| 6,899,735 B2 * | 5/2005 | Coates et al. ............. 623/17.16 |
| 6,936,071 B1 * | 8/2005 | Marnay et al. ........... 623/17.15 |
| 6,994,727 B2 | 2/2006 | Khandkar et al. |
| 7,060,097 B2 | 6/2006 | Fraser et al. |
| 2001/0020185 A1 | 9/2001 | Ray |
| 2002/0143343 A1 | 10/2002 | Castro |
| 2003/0028249 A1 | 2/2003 | Baccelli et al. |
| 2003/0109928 A1 | 6/2003 | Pasquet et al. |
| 2003/0187506 A1 | 10/2003 | Ross et al. |
| 2003/0220691 A1 | 11/2003 | Songer et al. |
| 2004/0002761 A1 | 1/2004 | Rogers et al. |
| 2004/0010316 A1 | 1/2004 | William et al. |
| 2004/0034423 A1 | 2/2004 | Lyons et al. |
| 2004/0073309 A1 | 4/2004 | Bianchi et al. |
| 2004/0073311 A1 | 4/2004 | Ferree |
| 2004/0093082 A1 | 5/2004 | Ferree |
| 2004/0111160 A1 | 6/2004 | Evans et al. |
| 2004/0117022 A1 | 6/2004 | Marnay et al. |
| 2004/0133278 A1 | 7/2004 | Marino et al. |
| 2004/0143332 A1 | 7/2004 | Krueger et al. |
| 2004/0148029 A1 | 7/2004 | Bianchi et al. |
| 2004/0162617 A1 | 8/2004 | Zucherman et al. |
| 2004/0193273 A1 | 9/2004 | Huang |
| 2004/0243238 A1 | 12/2004 | Arnin et al. |
| 2004/0243240 A1 * | 12/2004 | Beaurain et al. ......... 623/17.14 |
| 2005/0027359 A1 | 2/2005 | Mashburn |
| 2005/0027363 A1 | 2/2005 | Gordon |
| 2005/0060034 A1 | 3/2005 | Berry et al. |
| 2005/0065611 A1 | 3/2005 | Huppert et al. |
| 2005/0085917 A1 | 4/2005 | Marnay et al. |
| 2005/0149189 A1 | 7/2005 | Mokhtar et al. |
| 2005/0197706 A1 | 9/2005 | Hovorka et al. |
| 2005/0246024 A1 | 11/2005 | Zeegers |
| 2006/0041314 A1 | 2/2006 | Millard |
| 2006/0069437 A1 | 3/2006 | Weber |
| 2006/0122703 A1 * | 6/2006 | Aebi et al. ............... 623/17.15 |

FOREIGN PATENT DOCUMENTS

| | | |
|---|---|---|
| DE | 2263842 A | 7/1974 |
| DE | 2804936 | 8/1979 |
| DE | 3023353 | 4/1981 |
| DE | 3023353 A | 4/1981 |
| DE | 8912648 U | 11/1990 |
| DE | 20310432 U | 9/2003 |
| DE | 20310433 U | 9/2003 |
| EP | 42271 | 12/1981 |
| EP | 176728 | 4/1986 |
| EP | 0298235 A | 1/1989 |
| EP | 0317972 A | 5/1989 |
| EP | 333990 | 9/1989 |
| EP | 0333990 A | 9/1989 |
| EP | 0356112 | 2/1990 |
| EP | 0512529 A | 11/1992 |
| EP | 0560141 A | 9/1993 |
| EP | 0566810 A1 | 10/1993 |
| EP | 0566810 B1 | 5/1996 |
| EP | 0747025 A1 | 12/1996 |
| EP | 0955021 A | 11/1999 |
| FR | 2124815 | 9/1972 |
| FR | 2124815 A | 9/1972 |
| FR | 2372622 | 6/1978 |
| FR | 2632516 A | 12/1989 |
| FR | 2659226 A | 9/1991 |
| FR | 2718635 | 10/1995 |
| FR | 2718635 A1 | 3/1996 |
| FR | 2723841 | 3/1996 |
| FR | 2724108 A | 3/1996 |
| FR | 2730159 A1 | 8/1996 |
| FR | 2737656 | 2/1997 |
| FR | 2737656 A | 2/1997 |
| FR | 2787021 A | 6/2000 |
| FR | 2824261 | 11/2002 |
| FR | 2831796 | 5/2003 |
| FR | 2846550 | 5/2004 |
| FR | 2865629 | 8/2005 |
| FR | 2865630 A1 | 8/2005 |
| FR | 2869528 | 11/2005 |
| JP | 2261446 | 10/1990 |
| WO | WO9011740 A | 10/1990 |
| WO | WO9113598 A | 9/1991 |
| WO | WO9301771 A | 2/1993 |
| WO | WO9404100 | 3/1994 |
| WO | WO9909914 | 3/1999 |
| WO | WO9956675 A | 11/1999 |
| WO | WO0053127 A | 9/2000 |
| WO | WO0074606 A | 12/2000 |
| WO | WO0101893 A | 1/2001 |
| WO | WO0119295 A | 3/2001 |
| WO | WO02089701 A2 | 11/2002 |
| WO | WO03039400 A2 | 5/2003 |
| WO | WO03059212 A | 7/2003 |
| WO | WO03075804 A | 9/2003 |
| WO | WO2004041129 A1 | 5/2004 |
| WO | WO2005074839 | 8/2005 |
| WO | WO2005104996 | 11/2005 |

OTHER PUBLICATIONS

A Multicenter Retrospective Study of the Clinical Results of the LINK SB Charite Intervertebral Prosthesis, S. L. Griffith, PhD, A. P. Shelokov, MD, K. Buttner-Janz, MD, Jean-Phillipe LeMaire, MD and W. S. Zeegers, MD, Spine, vol. 19, No. 16, pp. 1842-1849, Mar. 21, 1994.

A New Technique for the Three-Dimensional Study of the Spine in Vitro and In Vivo by Using a Motion-Analysis System, X. Liu, G.

Fabry, K. Labey, L. Van Den Berghe, R. Van Audekercke, G. Molenaers, P. Moens, Journal of Spinal Disorders, vol. 10, No. 4, pp. 329-338, Jan. 30, 1997.

Alternatives to Spinal Fusion, J. P. Kostuik, Spinal Fusion, vol. 29, No. 4, Oct. 1998, pp. 701-415.

Centrode Patterns and Segmental Instability in Degenerative Disc Disease, S.D. Gertzban, MD, FRCSC, J. Seligman, MD, R. Holtby, MD, K.H. Chan, MD, A. Kapasouri, BSc, M. Tile, MD, BSc, (MED), FRCS ©, and B. Cruickshank, MD, FRCPath, Spine, vol. 10., No. 3, pp. 257-261, Jan. 21, 1984.

Clinical Biomechanics of the Spine, A. A. White III, M. M. Panjabi, pp. 128-130, 2nd Edition, J.B. Lippincott Co., 1990.

Computer Analysis of Spinal Segment Motion in Degenerative Disc Disease With and Without Axial Loading, J.V. Seligman, S.D. Gertzbein, M. Tile, A., Kapasouri, Spine, vol. 9., No. 6, pp. 566-573, Dec. 31, 1983.

FR 2 718 635 Preliminary Search Report, National Institute of Industrial Property (France), Jan. 16, 1995.

2 730 159 Preliminary Search Report, National Institute of Industrial Property (France), Sep. 29, 1995.

FR 2 824 261 Preliminary Search Report, National Institute of Industrial Property (France), Feb. 25, 2002.

FR 2 831 796 Prelinimary Search Report, National Institute of Industrial Property (France), Aug. 2, 2002.

FR 2 846 550 Prelinimary Search Report, National Institute of Industrial Property (France), Jul. 10, 2003.

FR 2 865 629 Preliminary Search Report, National Institute of Industrial Property (France), Sep. 14, 2004.

FR 2 865 630 Prelinimary Search Report, National Institute of Industrial Property (France), Jan. 12, 2005.

FR 2 869 528 Preliminary Search Report, National Institute of Industrial Property (France), Dec. 13, 2004.

Instantantaneous Axis of Rotation as a Function of the Three Columns of the Spine, T. R. Haher, MD, M. O'Brien, MD, W. T. Felmly, MD, D. Welin, MD, G. Perrier, MD., J. Choueka, MD, V. Devlin, MD, A. Vassiliou, ME, and G. Chow, MS, Spine, vol. 17, No. 6, pp. S149-S154, Jan. 9, 1992.

Instantantaneous Axis of Rotation of the Lumbar Intervertebral Joints, M. J. Pearcy, H. Bogduk, Spine, vol. 13, No. 9, pp. 1033-1041, Nov. 15, 1987.

Mobidisc (website) 1 page, www.ldrmedical.fr/mobidisc.htm, Sep. 19, 2004.

Motion Characteristics of the Normal Lumbar Spine in Young Adults: Instantaneous of Axis of Rotation and Vertebral Center Motion Analysis, T. Yoshioka, H. Tsuji, N. Hirano and S. Sainoh, Journal of Spinal Disorders, vol. 3, No. 2, pp. 103-113, 1990.

PCT/IB02/02998 International Search Report, EPO, Sep. 16, 2003.
PCT/IB02/04642 International Search Report, EPO, Jul. 2, 2003.
PCT/IB05/00280 International Search Report, EPO, Jun. 24, 2005.
PCT/IB05/01151 International Search Report, EPO, Sep. 12, 2005.
PCT/IB03/04872 International Search Report, EPO, Mar. 3, 2004.
PCT/IB02/02998 International Preliminary Examination Report, EPO, Dec. 22, 2003.
PCT/IB02/04642 International Preliminary Examination Report, EPO, Apr. 1, 2004.
PCT/IB03/04872 International Preliminary Examination Report, EPO, Mar. 1, 2005.

Relocation of the Bending Axis During Flexion-Extension of Lumbar Intervertebral Discs and its Implications for Prolapse, J.A. Klein and D.W.L. Hukins,Spine, vol. 8, No. 6, pp. 659-664, Nov. 18, 1982.

The Effect of the Three Columns of the Spine on the Instantaneous Axis of Rotation in Flexion and Extension, T. R. Haher, M. Bergman, M. O'Brien, W. T. Felmly, J. Choueka, D. Welin, G. Chow, A. Vassiliou, Spine, vol. 16, No. 8, pp. S312-S318, Apr. 16, 1991.

* cited by examiner

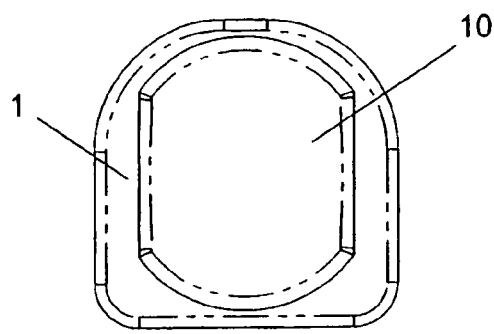
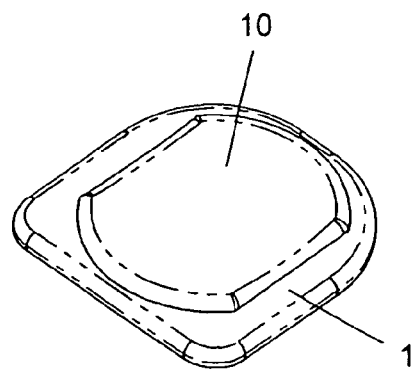
Figure 1a
Figure 1b
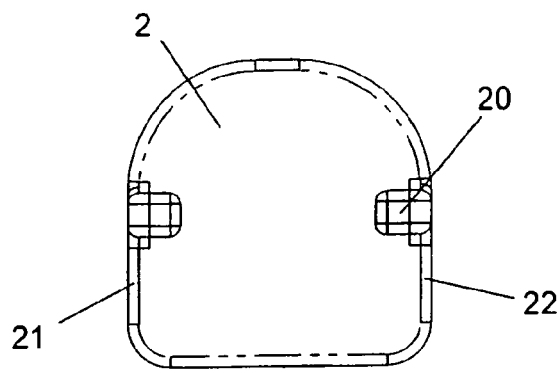
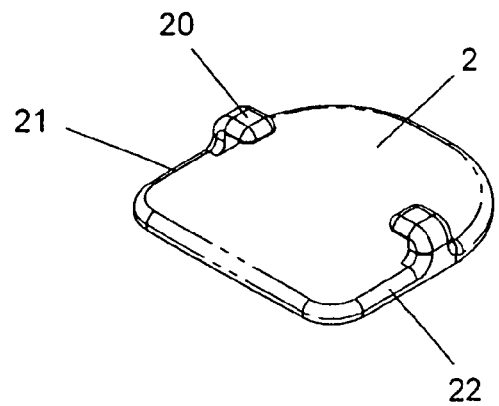
Figure 2a
Figure 2b
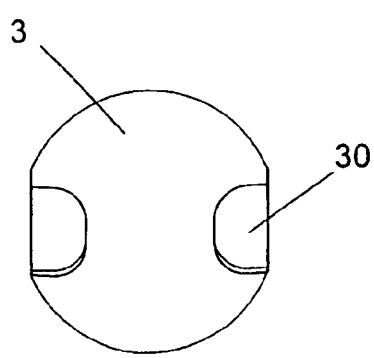
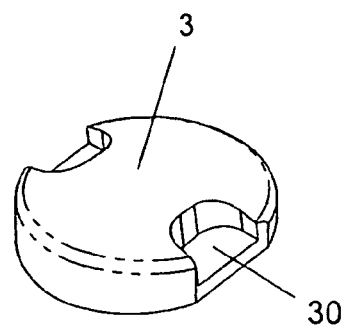
Figure 3a
Figure 3b

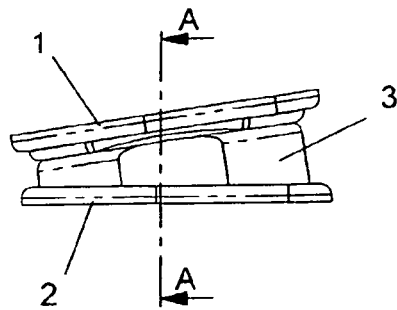
Figure 6a
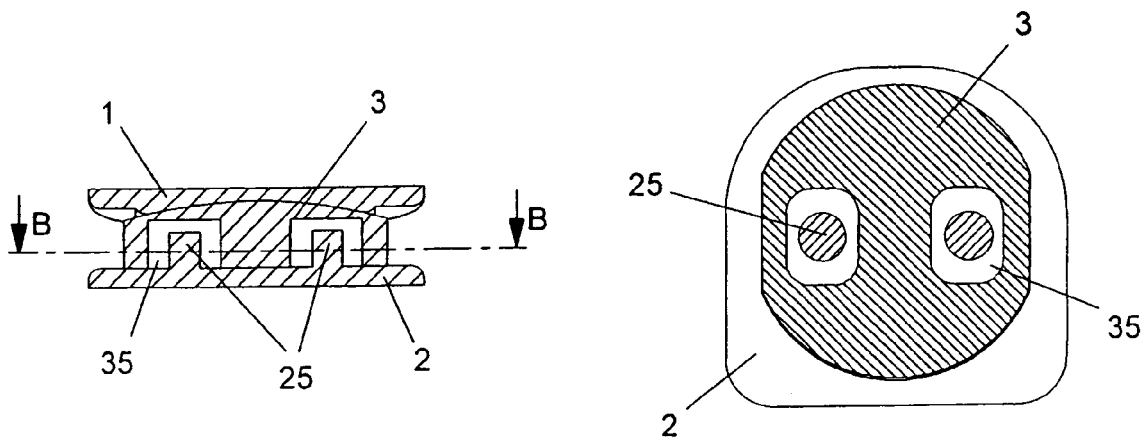
Figure 6b
Figure 6c
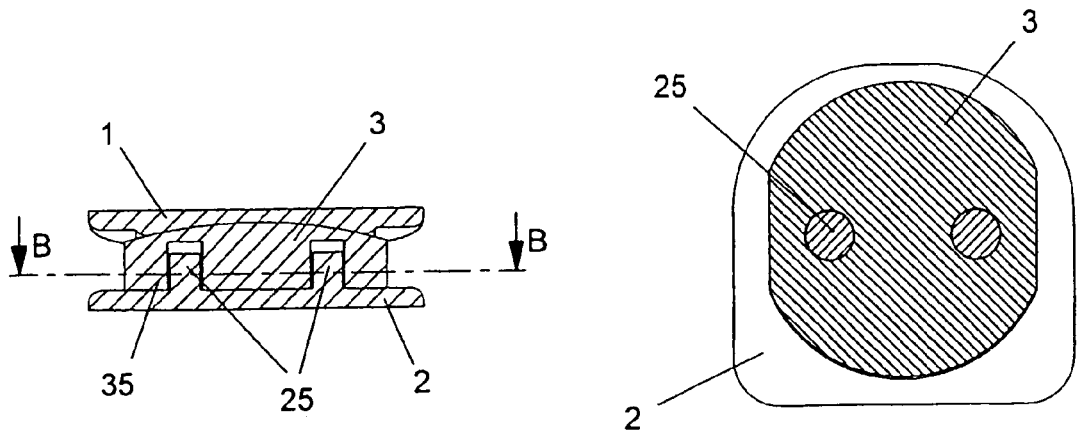
Figure 6d
Figure 6e

INTERVERTEBRAL DISC PROSTHESIS

The present invention relates to an intervertebral disk prosthesis, intended to substitute the fibrocartilaginous disks joining the vertebrae in the spinal column, particularly on the cervical spine.

Various types of prosthesis are known in the prior art. Some of these prostheses, either because they are made of compressible material or because they allow excessive movement of the different constituent parts of the prosthesis with respect to each other, may induce relatively easily the ejection of at least one part of the prosthesis outside the vertebrae, which is not desirable for the patient.

The purpose of the present invention is to remedy some drawbacks of the prior art by proposing a simple intervertebral disk prosthesis which makes it possible to limit the movements of the different constituent parts of the prosthesis with respect to each other.

This purpose is achieved by an intervertebral disk prosthesis comprising at least three parts including a first plate, referred to as the upper plate, a second plate, referred to as the lower plate, and a core, the upper surface of the core being in contact with at least part of the lower surface of the upper plate and the lower surface of the core being in contact with at least part of the upper surface of the lower plate, and the lower plate being movable at least with respect to the core, characterised in that there are cooperation means between the lower plate and the core, so as to limit or eliminate translation movements of the core with respect to the lower plate, along an axis substantially parallel to the lower plate, and to limit or eliminate rotation movements of the core with respect to the lower plate, around an axis substantially perpendicular to the lower plate, the planes passing through the upper and lower plates forming a substantially constant angle.

According to another feature, the lower plate comprises male means cooperating with female means of the core.

According to another feature, the lower plate comprises female means cooperating with male means of the core.

According to another feature, the angle is obtained in that the core forms an acute angle in the front-rear direction.

According to another feature, the same plates can be assembled with cores of different thicknesses.

According to another feature, the angle between the upper and lower plates is between 0° and 15°.

According to another feature the core is movable with respect to the upper and/or lower plates, which makes it possible to compensate for positioning defects of the three parts of the prosthesis with respect to each other.

According to another feature, at least part of the lower surface of the upper plate is concave and complementary to the upper surface of the core.

According to another feature, the dimensions of each male means are slightly less than those of each female means so as to enable a slight clearance between the core and the lower plate.

According to another feature, the dimensions of each male means are substantially the same as those of each female means so as to prevent any clearance between the core and the lower plate.

According to another feature, the male means of the lower plate are two pins curved towards the inside of the prosthesis and located opposite each other on two edges of the prosthesis, and in that the female means of the core are two recesses.

According to another feature, at least one of the pins is replaced by a lug equipped with a drilling whereon a tag is fixed using a dowel entering the drilling.

According to another feature, the male means of the lower plate are two dowel pins located in the vicinity of the centre of the lower plate, and in that the female means of the core are two wells.

According to another feature, the male means of the lower plate are two walls located opposite each other in the vicinity of two edges of the prosthesis, and in that the female means of the core are recesses.

According to another feature, the male means of the lower plate are a rib located at the centre of the prosthesis, and in that the female means of the core are a groove.

According to another feature, the core is made of polyethylene.

According to another feature, the lower plate comprises one or more openings in the vicinity of its front side, provided to receive prosthesis anchoring means in a vertebra.

According to another feature, the opening of the lower plate is rectangular, and in that the anchoring means consist of a body, forming an acute angle with the lower plate, and a head.

According to another feature, the openings of the lower plate are circular, and in that the anchoring means are nail-shaped.

According to another feature, the upper plate is convex on at least part of its upper surface to fit into the shape of the vertebrae.

Figure 9B:
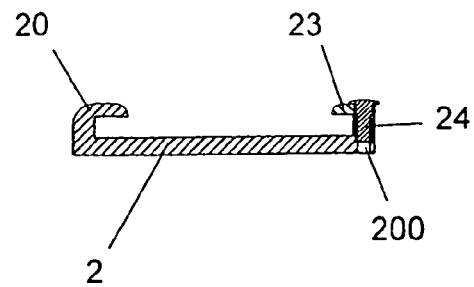
Figure 4A:
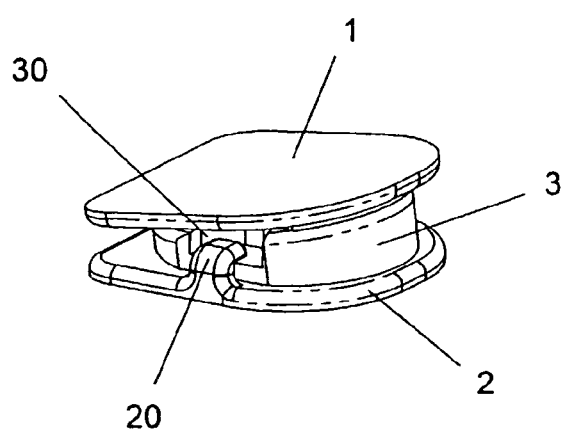
Figure 4B:
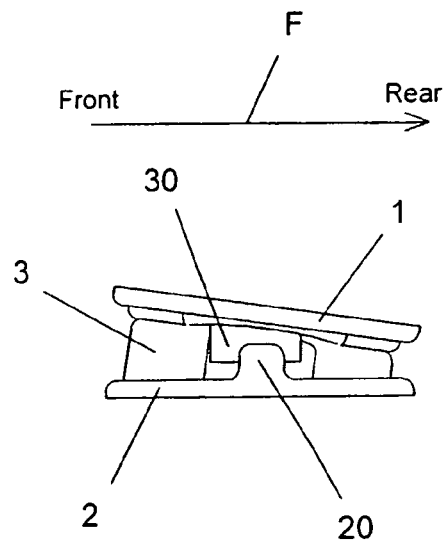
Figure 5A:
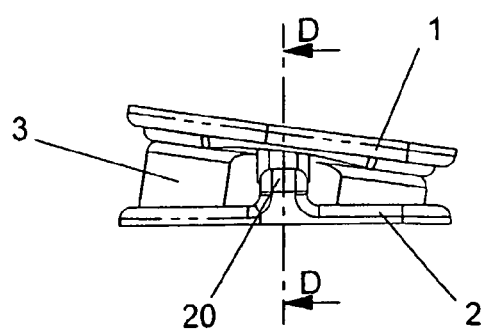
Figure 7A:
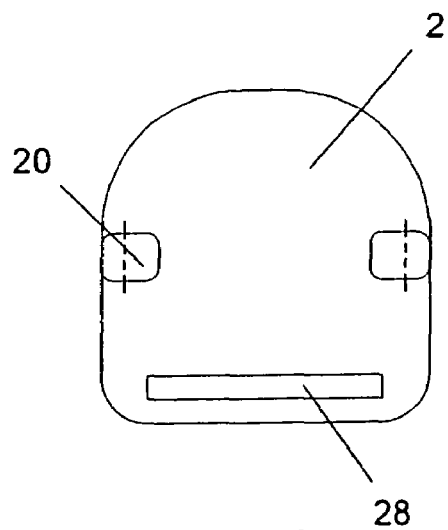
Figure 7B:
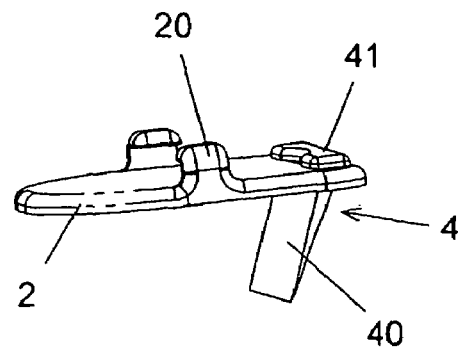
Figure 8A:
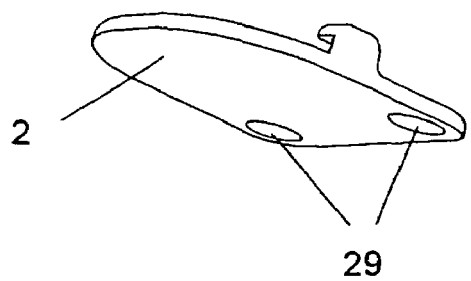
Figure 8B:
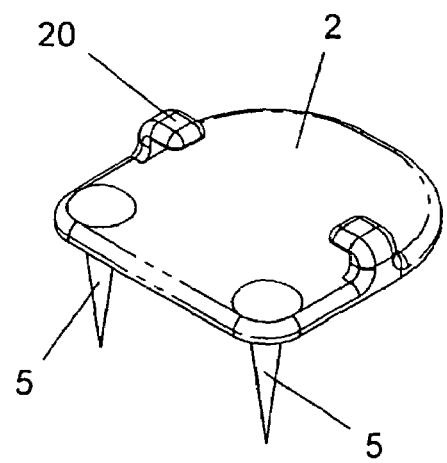
Figure 10A:
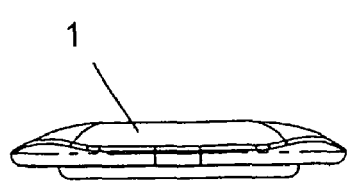
Figure 10B:
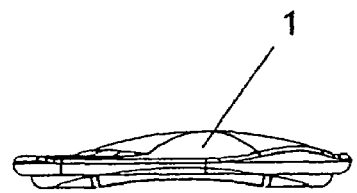

Other features and advantages of the present invention will be seen more clearly upon reading the description below, with reference to the appended figures, wherein:

FIGS. 1a and 1b respectively represent a bottom view and a perspective bottom view of the upper plate according to one embodiment, FIGS. 2a and 2b respectively represent a top view and a perspective top view of the lower plate according to one embodiment, FIGS. 3a and 3b respectively represent a top view and a perspective top view of the core according to one embodiment, FIGS. 4a and 4b respectively represent a perspective top view and a side view of the intervertebral disk prosthesis according to the embodiment of FIGS. 1a, 1b, 2a, 2b, 3a and 3b, FIGS. 5a and 5b respectively represent a side view and a sectional view along the plane D-D of FIG. 5a of the intervertebral disk prosthesis according to a second embodiment, FIG. 6a represents a side view of the intervertebral disk prosthesis according to a third embodiment, FIGS. 6b and 6d represent a sectional view along the plane A-A of FIG. 6a, the core having, respectively, a slight clearance and no clearance with respect to the lower plate, FIGS. 6c and 6e represent a sectional view along the plane B-B of FIGS. 6b and 6d, respectively, of the intervertebral disk prosthesis, FIGS. 7a and 8a respectively represent a top view and perspective bottom view of the lower plate according to two other embodiments, FIGS. 7b and 8b respectively represent a perspective side view and a perspective top view of the lower plate of FIGS. 7a and 8a, respectively, wherein prosthesis anchoring means are inserted according to two different embodiments, FIG. 9a represents a top view of the lower plate according to a fourth embodiment, FIG. 9b represents a sectional view of the lower plate along the plane plan C-C of FIG. 9a, FIGS. 10a and 10b respectively represent a rear and side view of the upper plate according to another embodiment.

The intervertebral disk prosthesis according to the invention is constituted of an upper plate 1 which is articulated with respect to a lower plate 2 by means of a core 3, as can particularly be seen in FIGS. 4a, 4b, 5a and 6a. One advantage of the prosthesis according to the invention is that it comprises simple parts which can be designed so that the prosthesis is fitted on the cervical spine.

The upper plate 1, particularly visible in FIGS. 1a and 1b, is slightly concave on at least part 10 of its lower surface, so as to fit with the slightly convex upper surface of the core 3. The upper surface of the core 3 is complementary to the concave part 10 of the upper plate 1, enabling movement between the upper plate 1 and the core 3.

In an alternative embodiment, part of the upper surface of the upper plate 1 is convex, as shown in FIGS. 10a and 10b, in order to fit better onto the vertebra whereon the prosthesis is to be fitted, the bottom of the vertebrae being concave. In this case, the convex part of the upper plate 1 is located in the front part of the upper plate, as can particularly be seen in FIG. 10b.

The lower plate 2 is substantially plane. In effect, its lower surface does not need to be convex or concave since the top of the vertebrae is substantially flat. In the embodiment of FIGS. 2a, 2b, 7a and 8a, the lower plate 2 comprises two pins 20 located opposite, each other on two substantially parallel edges 21, 22 of the lower plate 2. Each pin 20 is curved towards the inside of the prosthesis and can thus enter recesses 30 located on the core 3. The core 3, particularly visible in FIGS. 3a and 3b, comprises a substantially plane lower surface, provided to fit onto the lower plate 2. The core 3 is thin (for example 3 mm thick) for a cervical prosthesis or thicker (for example 15 mm) for a lumbar prosthesis.

In the embodiment of FIGS. 3a, 3b, 4a and 4b, the dimensions of each recess 30 of the core 3 are slightly greater than those of each pin 20 of the lower plate 2 so as to limit the clearance of the core 3 with respect to the lower plate 2, both in translation along an axis substantially parallel with the lower plate 2, and in rotation around an axis substantially perpendicular to the lower plate 2. The movement between the upper plate 1 and the core 3, as well as the clearance of the core 3 with respect to the lower plate 2, thus enable the patient to move and, if required, compensate for prosthesis positioning defects. This clearance also offers the advantage of preventing premature wear due to the stress applied to the prosthesis.

Figure 5B:
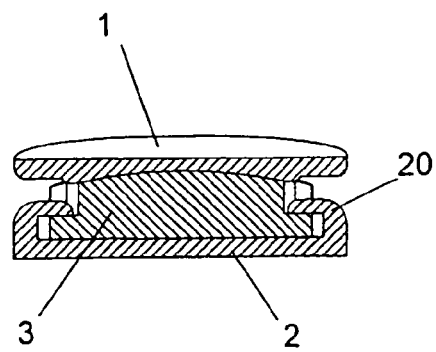

In the embodiment of FIGS. 5a and 5b, the dimensions of each recess 30 of the core 3 are substantially the same as those of each pin 20 of the lower plate 2, so as to prevent any clearance of the core 3 with respect to the lower plate 2, both in translation and rotation. In the latter case, the only movement of the prosthesis authorised is that of the upper plate 1 with respect to the core 3.

In the embodiment in FIGS. 9a and 9b, one of the pins 20 is replaced by a lug equipped with a drilling 200. A tag 23 fixes on the lug by means of a dowel 24 entering the drilling 200. In an alternative embodiment, both pins are replaced by a lug whereon a tag 23 is fixed.

In the embodiment of FIGS. 6a, 6b, 6c, 6d and 6e, the lower plate 2 does not comprise any pins 20 but two dowel pins 25 located in the vicinity of the centre of the lower plate 2. In this case, the core 3, by complementarity, does not comprise any recesses 30, but two wells 35 under its lower surface. The dimensions of the dowel pins 25 of the lower plate 2 and of the wells 35 of the core 3 are such that, in the alternative embodiment represented in FIGS. 6b and 6c, a slight clearance in translation and rotation is permitted, and in the alternative embodiment represented in FIGS. 6d and 6e, no clearance is permitted.

In another embodiment, not shown, the lower plate 2 comprises a rib on its upper surface and no pins 20 or dowel pins 25. The core 3, by complementarity, comprises a groove under its lower surface. The dimensions of the rib of the lower plate and the groove of the core are such that, in one alternative embodiment, a slight clearance in translation and rotation is permitted, and in another alternative embodiment, no clearance is permitted.

In another embodiment not shown, the lower plate 2 comprises, instead of the pins 20, two walls, arranged opposite each other, in the vicinity of two substantially parallel edges 21, 22 of the lower plate, but further in the prosthesis than the pins 20. The core 3 comprises complementary recesses with respect to the walls. The dimensions of each recess of the core in this embodiment are, either slightly greater, or substantially the same as those of each wall of the lower plate, so as to enable a slight clearance in translation and rotation or not.

In a further embodiment not shown, the female components are located on the lower plate and the male components on the core.

The intervertebral disk prosthesis according to the invention particularly makes it possible to correct lordosis defects and to add lordosis to the spine, for example the cervical spine. Therefore, the presence of an acute angle in the front-rear direction F, FIG. 4b, between the upper plate 1 and the lower plate 2 of the prosthesis is necessary. For example, this angle is between 0° and 15°. To adjust the angle required according to the patient, it is simply necessary to select a core 3 with a suitable angle between the mean plane representing its upper surface and the plane passing through its lower surface.

When the female components are located on the lower plates and the male components on the core, the lordotic core, in that it forms an acute angle in the front-rear direction, may then be integral with the plate by a projection entering a cavity or opening of the lower plate.

The inclination of the prostheses known in the prior art is obtained, either by the shape of the upper plate, when the core is flat, or by the position of the upper plate with respect to the core, when said core is convex. With respect to the first case of the prior art mentioned here, the machining of the prosthesis according to the present invention is more economical since the core is composed of a less expensive material (for example, polyethylene) than that composing the plates. With respect to the second case of the prior art mentioned here, the core of the present invention is not liable to be ejected outside the prosthesis since the angle between the plates is substantially constant when the prosthesis is in place.

If surgeons require a determined lordosis for one patient, they will select a core 3 allowing no clearance with respect to the lower plate 2. On the other hand, if they simply require the lordosis to remain within a range of values, they will select a core allowing a slight clearance in translation and rotation with respect to the lower plate 2.

The intervertebral disk prosthesis according to the invention may, in one alternative embodiment, represented in FIGS. 7a, 7b, 8a and 8b, be anchored in the spinal column to prevent the prosthesis from migrating under the effect of the transversal resultant of the force exerted by the spinal column on the prosthesis in place, which increases with the lordosis. In this case, the lower plate 2 comprises one or more openings 28, 29 located in the vicinity of the rear side of the prosthesis, making it possible to receive anchoring means 4, 5.

In this way, in the case of FIGS. 7a and 7b, the opening 28 of the lower plate 2 is rectangular and the anchoring means 4 is constituted of a body 40 and a head 41. The dimensions of the head 41 are slightly greater than those of the opening 28 of the lower plate 2, such that, once the anchoring means 4 are in place in a vertebra, the lower plate 2 is sandwiched between the head 41 of the anchoring means 4 and said vertebra. An angle, less than or equal to 90°, is comprised between the body 40 of the anchoring means 4 and the lower plate 2.

In the case of FIGS. 8a and 8b, two circular openings 29 are comprised in the lower plate 2 and the anchoring means 5 are nail-shaped, with a head of greater dimensions than those of the openings 29 to make it possible to sandwich the lower plate 2 between the head of the anchoring means 5 and the vertebra whereon the prosthesis is anchored.

It should be clear to those skilled in art that the present invention enables embodiments in numerous other specific forms without deviating from the scope of the invention as claimed. Consequently, the present embodiments must be considered as illustrations, but may be modified in the field defined by the scope of the attached claims, and the invention must not be limited to the details given above.

The invention claimed is:

1. Intervertebral disc prosthesis comprising an upper plate, a lower plate, and a core, a curved upper surface of the core being in contact with at least part of a curved lower surface of the upper plate and a lower surface of the core being in contact with at least part of an upper surface of the lower plate with an angle between respective planes of the upper and lower plates being obtained by the core having an acute angle in a front-rear direction, and the upper plate being moveable at least with respect to the core and the core being movable in translation and rotation with respect to the lower plate, and in which there are cooperation means not located in the middle of the core between the lower plate and the core, so as to limit translation movements of the core with respect to the lower plate around an axis substantially parallel to the lower plate when the intervertebral disc prosthesis is assembled, and to limit or eliminate rotation movements of the core with respect to the lower plate around an axis substantially perpendicular to the lower plate when the intervertebral disc prosthesis is assembled, in which the lower plate comprises male means cooperating with female means of the core and the male means of the lower plate are two pins curved towards the inside of the prosthesis and located opposite each other on two edges of the prosthesis, and in that the female means of the core are two recesses.

2. Intervertebral disc prosthesis according to claim 1, in which the lower plate and the upper plate are assembled with a second core rather than the core and the second core has a thickness that differs from the thickness of the core.

3. Intervertebral disc prosthesis according to claim 2, in which the angle between the upper and lower plates is between 0° and 15°.

4. Intervertebral disc prosthesis according to claim 1, in which the core is movable with respect to the upper and/or lower plates, to compensate for relative positioning defects between the upper plate, the lower plate and the core of the prosthesis.

5. Intervertebral disc prosthesis according to claim 1, in which at least part of the lower surface of the upper plate is concave and complementary to the upper surface of the core.

6. Intervertebral disc prosthesis according to any one of claim 1, in which the dimensions of each male means are less than those of each female means so as to enable a slight clearance between the core and the lower plate.

7. Intervertebral disc prosthesis according to any one of claim 1, in which the dimensions of each male means are substantially the same as those of each female means so as to inhibit clearance between the core and the lower plate.

8. Intervertebral disc prosthesis according to claim 1, in which at least one of the pins is replaced by a lug equipped with a drilling whereon a tag using a dowel entering the drilling.

9. Intervertebral disc prosthesis according to claim 1, in which the core is made of polyethylene.

10. Intervertebral disc prosthesis according to claim 1, in which the lower plate comprises one or more openings along its front side, provided to receive prosthesis anchoring means in a vertebra.

11. Intervertebral disc prosthesis according to claim 10, in which the opening of the lower plate is rectangular, and in which the anchoring means comprise a body, forming an acute angle with the lower plate, and a head.

12. Intervertebral disc prosthesis according to claim 10, in which the openings of the lower plate are circular, and in which the anchoring means are nail-shaped.

13. Intervertebral disc prosthesis according to claim 1, in which the upper plate is convex on at least part of its upper surface to fit into the shape of the vertebrae.

14. An intervertebral disc prosthesis for substitution of a fibrocartilaginous disc between adjacent vertebra in a spinal column comprising:
an upper plate having a curved lower surface;
a lower plate having an upper surface;
a core having an upper surface and a lower surface,
the upper surface of the core being curved and configured for contact with at least part of the curved lower surface of the upper plate and
the lower surface of the core being configured for contact with at least part of the upper surface of the lower plate, said contact of the lower surface of the core with at least part of the upper surface of the lower plate being configured for translation movements of the core with respect to the lower plate along an axis substantially parallel to the upper surface of the lower plate and for rotation movements of the core with respect to the lower plate around an axis substantially perpendicular to the upper surface of the lower plate when the intervertebral disc prosthesis is assembled; and
a stop comprising a male portion disposed on the lower plate and a female portion disposed on the core, the male portion and the female portion each located along an edge of the prosthesis, and the male portion and the female portion each configured to limit translation movements of the core with respect to lower plate and rotation movements of the core with respect to the lower plate, in which the male portion is a tag fixed by a dowel.

15. An intervertebral disc prosthesis according to claim 14 in which the upper surface of the core is convex and the lower surface of the upper plate is concave, and the lower surface of the core and the upper surface of the lower plate are each substantially planar.

16. An intervertebral disc prosthesis according to claim 15 in which the upper plate has an upper surface that is convex and the lower plate has a lower surface that is substantially planar.

17. An intervertebral disc prosthesis according to claim 16 further comprising anchors configured to engage an adjacent vertebra.

18. An intervertebral disc prosthesis according to claim 17 in which the anchors are disposed on opposite sides of the prosthesis.

19. An intervertebral disc prosthesis according to claim 14, in which the female portion is a recess.

20. An intervertebral disc prosthesis according to claim 19 in which the recess is a groove.

21. An intervertebral disc prosthesis according to claim 14 in which the core forms an acute angle in a front-rear direction.

22. An intervertebral disc prosthesis according to claim 14 in which the core can have different thicknesses.

23. An intervertebral disc prosthesis for substitution of a fibrocartilaginous disc between adjacent vertebra in a spinal column comprising:

an upper plate having a curved lower surface;

a lower plate having an upper surface;

a core having an upper surface and a lower surface, the upper surface of the core being curved and configured for contact with at least part of the curved lower surface of the upper plate and the lower surface of the core being configured for contact with at least part of the upper surface of the lower plate, said contact of the lower surface of the cote with at least part of the upper surface of the lower plate being configured for translation movements of the core with respect to the lower plate along an axis substantially parallel to the upper surface of the lower plate and for rotation movements of the core with respect to the lower plate around an axis substantially perpendicular to the upper surface of the lower plate when the intervertebral disc prosthesis is assembled; and a stop comprising a male portion disposed on the lower plate and a female portion disposed on the core, the male portion and the female portion each located along an edge of the prosthesis, and the male portion and the female portion each configured to limit translation movements of the core with respect to lower plate and rotation movements of the core with respect to the lower plate, in which the male portion is an inwardly curved pin.

24. An intervertebral disc prosthesis according to claim 23 in which the upper surface of the core is convex and the lower surface of the upper plate is concave, and the lower surface of the core and the upper surface of the lower plate are each substantially planar.

25. An intervertebral disc prosthesis according to claim 24 in which the upper plate has an upper surface that is convex and the lower plate has a lower surface that is substantially planar.

26. An intervertebral disc prosthesis according to claim 25 further comprising anchors configured to engage an adjacent vertebra.

27. An intervertebral disc prosthesis according to claim 26 in which the anchors are disposed on opposite sides of the prosthesis.

28. An intervertebral disc prosthesis according to claim 23 in which the female portion is a recess.

29. An intervertebral disc prosthesis according to claim 28 in which the recess is a groove.

30. An intervertebral disc prosthesis according to claim 23 in which the core forms an acute angle in a front-rear direction.

31. An intervertebral disc prosthesis according to claim 23 in which the core can have different thicknesses.

* * * * *